United States Patent
Tucker et al.

(10) Patent No.: US 9,084,544 B2
(45) Date of Patent: Jul. 21, 2015

(54) NERVE LOCATOR

(75) Inventors: Arthur Tucker, Leytonstone (GB); Duncan Bain, Kings Langley (GB)

(73) Assignee: Sky Medical Technology Ltd., Cheshire (GB)

(*) Notice: Subject to any disclaimer, the term of this patent is extended or adjusted under 35 U.S.C. 154(b) by 0 days.

(21) Appl. No.: 14/006,879

(22) PCT Filed: Mar. 27, 2012

(86) PCT No.: PCT/GB2012/050677
§ 371 (c)(1),
(2), (4) Date: Nov. 6, 2013

(87) PCT Pub. No.: WO2012/131357
PCT Pub. Date: Oct. 4, 2012

(65) Prior Publication Data
US 2014/0058242 A1 Feb. 27, 2014

(30) Foreign Application Priority Data
Mar. 31, 2011 (GB) .................................. 1105432.7

(51) Int. Cl.
*A61N 1/18* (2006.01)
*A61B 5/04* (2006.01)
*A61N 1/36* (2006.01)
*A61B 5/05* (2006.01)
*A61B 5/00* (2006.01)

(52) U.S. Cl.
CPC ............... *A61B 5/04001* (2013.01); *A61B 5/05* (2013.01); *A61B 5/4538* (2013.01); *A61B 5/4887* (2013.01); *A61N 1/36014* (2013.01)

(58) Field of Classification Search
CPC ..... A61N 1/04; A61N 1/0404; A61N 1/0456; A61N 1/0476; A61N 1/18; A61N 1/20; A61N 1/205; A61N 1/24; A61N 1/303; A61B 5/0404; A61B 5/0408
See application file for complete search history.

(56) References Cited

U.S. PATENT DOCUMENTS

2012/0053655 A1* 3/2012 Bain et al. ..................... 607/48

* cited by examiner

*Primary Examiner* — Christopher D Koharski
*Assistant Examiner* — Frances Oropeza
(74) *Attorney, Agent, or Firm* — Wolf, Greenfield & Sacks, P.C.

(57) ABSTRACT

A device for identifying appropriate nerve stimulation points on a patient is described, for use with an electrical stimulation device. In a first embodiment, the device includes electrodes located on a flexible substrate, a conductive gel layer overlying the electrodes, and a partially conductive removable cover overlying the gel layer. The device may be operated initially with the cover in place to allow reduced stimulation to identify a suitable nerve stimulation point. The cover may then be removed, and the device operated at the identified point. The cover may include perforations allowing the gel to contact the patient; or may be a sacrificial gel layer.

13 Claims, 2 Drawing Sheets

NERVE LOCATOR

CROSS-REFERENCE TO RELATED APPLICATIONS

This application is a national stage filing under 35 U.S.C. §371 of International Application No. PCT/GB2012/050677 filed Mar. 27, 2012, entitled NERVE LOCATOR, the entire content of which is incorporated by reference herein. International Application No. PCT/GB2012/050677 claims priority under 35 U.S.C. §119 (a)-(d) to United Kingdom Application No. GB 1105432.7, filed Mar. 31, 2011.

FIELD OF THE INVENTION

The present invention relates to a means whereby an appropriate stimulation point may be identified on a patient for use with transcutaneous electrical stimulation. Aspects of the invention relate to a modified device for electrical stimulation of a nerve of a patient, which device allows identification of an appropriate stimulation point and hence location of a nerve for such stimulation.

BACKGROUND TO THE INVENTION

Devices for transcutaneous electrical stimulation of nerves are described in international patent applications WO2006/054118 and WO2010/070332. The second of these describes a device including a flexible substrate on which are mounted positive and negative electrodes; a power supply connectable to the electrodes; and control means for activating the electrodes. The preferred embodiment of the device is in the form of an elongate "tongue" of flexible plastic which carries the electrodes (this is shown in FIG. 14 of WO2010/070332, reproduced here as FIG. 1). The device is intended for use in stimulating a nerve in the leg (specifically, the lateral and/or medial popliteal nerve) which innervates opposed leg muscles so as to cause isometric contraction of the muscles. This serves to activate the calf blood pump to encourage blood circulation in the patient. The device is intended for use in reducing the incidence of DVT, or for various other treatments (eg, enhancement of bone marrow perfusion, sports training and rehabilitation, peripheral arterial disease, among others). However, it will be apparent to the skilled person that this, and other similar devices, may be used to stimulate other areas of the body.

A key stage in using the device correctly is identifying the correct location for nerve stimulation. If the device is placed on the body incorrectly, then there may be reduced or even no stimulation of the correct nerve, such that the device will fail to operate as intended. In many patients it is relatively easy to identify the correct location for placement, since in general the position for optimum stimulation of the lateral or medial popliteal nerve will vary little between individuals. However there is of course some variation, and in some patients it may be more difficult to locate the correct position, or the correct position may differ more markedly from the norm. Accordingly, it would be desirable to have some way in which the location for nerve stimulation may be identified for using the device.

The device as described in WO2010/070332 and reproduced herein as FIG. 1 is not intended to be reusable. A preferred embodiment includes a layer of hydrogel or other electrically conductive gel which is located between the electrodes and the user's skin. The gel both provides electrical contact between the electrodes and the user, but also serves to adhere the device to the user. Moving and repositioning the device (for example, to identify the optimal location for nerve stimulation) would rapidly degrade the gel to the point that adhesion would be lost, and possibly also electrical contact. It is therefore not practical to identify the preferred location for the device simply by repeated moving and repositioning.

The patient could use two devices, one for identifying the correct location, which will allow the conductive gel to degrade, and a second working device for use once the correct location has been identified and marked. This approach is undesirable as it effectively discards one of the devices.

An alternative approach therefore may be to place an additional gel—for example, ultrasound gel—on the patient, thereby allowing easy repositioning and sliding of the device over the patient until the correct location has been identified. The correct location may be marked, and the ultrasound gel removed prior to the working device being put into position. However, this is complex and potentially messy, so is not preferred.

The present inventors have therefore designed a modified device which allows a single device to be used both for initially locating the preferred contact position on a patient, and for use as a working device.

SUMMARY OF THE INVENTION

According to a first aspect of the invention, there is provided a device for administering electrical stimulation to a patient, the device comprising a pair of electrodes located on a flexible substrate, a power supply connectable to the electrodes, and control means for actuating the electrodes, wherein the device further comprises a conductive gel layer overlying the electrodes, and a removable cover overlying the conductive gel layer, wherein the removable cover is at least partially conductive such that electrical contact may be formed in use between the electrodes and a patient when the cover is in place.

This allows the device to be used initially with the cover in place to identify the preferred location for placement of the device, without degrading the gel. The device may be placed on a patient with the cover in place, the electrodes actuated, and the device moved until the preferred location is found (for example, by observing muscle twitch as a result of the electrical contact between the electrodes and the patient via the cover). This location may then be marked, the cover removed, and the device replaced with the conductive gel contacting the patient.

Further, the device has the additional advantage that the cover protects the gel layer when the device is not in use, or is in transit.

The gel is preferably in a single piece overlying both electrodes, for ease of manufacture as well as structural integrity. We have determined that a single piece of gel may be used, based on the bulk resistivity of the material and geometry, so that leakage resistance is much greater than delivery resistance. Examples of gels which may be used include hydrogel or silicone.

Preferably the power supply and/or the control means are also located on the flexible substrate.

The substrate is preferably elongate, with the electrodes arranged along the substrate.

The substrate preferably comprises one or more registration marks, to allow a user to mark the location of the device prior to removal and replacement. The registration marks may be in the form of an indent or a notch or the like.

The cover is preferably a removable strip, and may conform to the shape of the substrate.

Preferably the cover is less conductive than the conductive gel.

The cover may be formed of a partially conductive material. For example a sheet material comprising a non-conductive polymer substrate loaded with a powder or granular conductive filler such as carbon, or metallic powder. This approach has been shown to produce partially conductive materials when the proportion of filler exceeds a certain percentage, which depends on the size and shape of the filler granules. Such materials are commercially available in sheet form.

Preferably the cover comprises perforations which allow a portion of the conductive gel to be contacted through the cover. This provides a partially conductive cover by virtue of allowing electrical flow through the gel to the patient when the cover is in place. However, the use of perforations prevents most of the possible current flow. In this preferred embodiment it is possible that some portion of the conductive gel may be degraded during the location phase, but the majority of the gel will be protected by the cover. Furthermore, the use of a perforated cover provides ease of manufacture and use, since conventional materials (for example, plastics or papers) may be used to produce the cover, and creation of perforations is relatively straightforward. Note that in this embodiment, the cover material itself need not be conductive; the partially conductive cover is made so due to the perforations removing the insulation barrier between gel and skin. This is a preferred embodiment because 1) conductivity is anisotropic (through the sheet, but not along it between electrodes), 2) conductivity can be achieved in selected zones if required, 3) can be produced much more cheaply than loaded substrate approach.

The cover may include a plurality of generally circular perforations overlying the electrode positions. Preferably however the perforations are generally uniformly distributed over the cover; this simplifies manufacturing. Preferably the perforations comprise no more than 50%, 40%, 30%, 25%, 20%, 15%, 10%, or 5% of the surface area of the cover.

Alternatively, the cover may be in the form of a plurality of sections (for example, strips) separated by gaps allowing the conductive gel to contact a user at the gaps.

Preferably the device in use is secured to the leg of a patient and used to provide electrical stimulation to the muscles. Preferably the electrodes are arranged to stimulate the lateral and/or medial popliteal nerves, which causes the calf muscles to contract. This in turn activates the calf musculovenous pump, in which blood circulation is promoted by muscle contraction, so serving to reduce the risk of thrombosis in the limb. Other musculovenous pumps include the foot pump, and the device may be used to stimulate this as well as, or instead of, the calf pump. The device is preferably used to induce isometric contraction of the muscles, such that the musculovenous pumps may be activated but limb movement from the stimulation is reduced or avoided.

Preferably the positive and negative electrodes are separated by 20-30 mm; we have found that this provides a preferred degree of stimulation.

The electrodes may be of different sizes; preferably the positive electrode is larger than the negative. This provides a higher charge density at the motor point, and greater capacitance overall. The electrodes may be silver electrodes. The electrodes may be continuous, or may include holes—for example, the electrodes may be solid electrodes, or may be in the form of a mesh.

The control means may be, for example, a PCB configured to activate the electrodes as appropriate. The power supply may be an electrical cell. The substrate is preferably flexible, but not stretchable—this reduces the risk of the electrodes cracking or breaking. For example, the substrate may be a thermoplastic elastomer.

The electrodes may be directly printed onto the substrate, by conventional printing means (for example pad or tampo printing). Similarly, conductive tracks may also be printed onto the substrate if desired.

The substrate may be in the form of an elongate strip or tongue, with the electrodes spaced along the strip. Such an arrangement may require a conductive track to be placed from the power supply to the further electrode, passing close to the nearer electrode. In such arrangements, the device may further comprise one or more insulative strips or regions arranged to separate the conductive track from the nearer electrode; insulative strips may also or instead be arranged along the edges of the strip to prevent current leaking outside the area of the strip. Alternatively, or in addition, the substrate may comprise a recessed groove within which a conductive track may be located; thereby serving to separate the track from the electrode.

The device may include a press button for activating or deactivating the device. The control means may be configured to provide a plurality of activation modes (for example, with different stimulation characteristics); the press button may be used to cycle through these modes. The device may include a display means, such as a light or an LED, to indicate the selected activation mode.

In certain embodiments the device may be disposable; for example, after a single use.

The device is intended to be sufficiently small and light—for example, less than 10 cm in length, and weighing less than 100 g, preferably less than 20 g—so as to be highly portable.

The cover may further comprise a lubricant coating to reduce friction between a user's skin and the cover when moving the device. The lubricant may be for example wax, oil, polymer, or the like. In certain embodiments, the cover may not include a lubricant coating, but the device may be used with an additional lubricant, for example, oils or gels may be applied to the cover or to the user before use.

In an alternative embodiment of the invention, the cover is in the form of a second conductive or partially conductive gel, of different composition to the first conductive gel. For example, the second gel may be less adhesive or may be less solid than the first. This allows the second gel to be used as a sacrificial gel layer for moving across a patient to identify the preferred location for stimulation. Once the preferred location is found and marked, the second gel is completely removed, and the first gel used to adhere the device to the user. However, this embodiment is not preferred.

The device may comprise an additional removable protective cover, preferably in the form of a protective strip, to cover the first cover. The additional cover is especially preferable when the first cover comprises perforations; in this way the gel which is accessible through the perforations may be protected during transit etc prior to use. Alternatively, or in addition, the devices may be packed and/or transported in pairs, with the strips facing one another. This serves to further protect the gel and the covers during transit.

Accordingly, a further aspect of the invention provides a package comprising a pair of devices as described herein, with the devices being placed such that the cover of one contacts the cover of the other.

An alternative solution to the problem of locating a preferred site for stimulation is the provision of a separate device for locating the site; once located, a device as described above or in WO2010/070332 may be used for electrical stimulation. The location device may comprise a rigid handle connected to a solid substrate, the substrate carrying a pair of electrodes; a power supply connectable to the electrodes; and control means for actuating the electrodes; a plurality of marking lugs for marking the location of the device on a user; wherein the electrodes are configured so as to correspond to the location of the electrodes on a separate device for electrically stimulating a user, and the marking lugs are arranged so as to mark predetermined points corresponding to predetermined points on the separate device.

Preferably the lugs may be actuated to mark the skin of a user; for example, the lugs may be extendable to contact the skin of a user, and/or may bear ink or other marking medium.

The location device may be provided in a kit comprising the location device and one or more of said separate devices.

BRIEF DESCRIPTION OF THE DRAWINGS

These and other aspects of the present invention will now be described by way of example only and with reference to the accompanying drawings, in which.

DETAILED DESCRIPTION OF THE DRAWINGS

Figure 1:
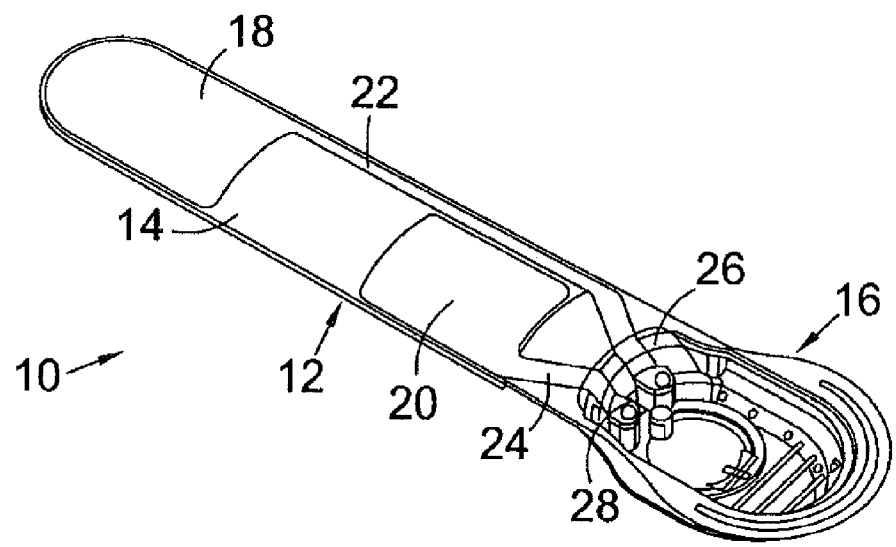
FIG. 1 shows a device as described in WO2010/070332.

FIG. 1 shows an embodiment of a device as described in WO2010/070332. The device 10 comprises a flexible, non-stretchable thermoplastic elastomer substrate 12 which includes an elongate tongue 14 at one end, and a moulded recess 16 at the other. On the tongue 14 are printed positive 18 and negative 20 electrodes. The positive is slightly larger than the negative. Each electrode includes a conductive track 22, 24 leading from the electrode to a respective contact point 26, 28 located in the recess 16. Not shown in the figure are an insulative strip arranged between the positive track 22 and the negative electrode 20, and similar strips at the edges of the tongue, to prevent unwanted leakage of current.

Within the recess 16 are placed an electrical cell (not shown), and a PCB (not shown) including suitable circuitry to control the electrodes. Together with the conductive tracks 22, 24 and contact points 26, 28, this forms a complete circuit. A plastic cover is then sonically welded over the recess 16 to seal the components. A layer of gel is then placed over the whole device 10; this provides an electrical contact with a user's limb and helps keep the device adhered to a user. The gel may be protected in transit by a peelable backing layer.

The outer surface of the recess 16 is formed with an integral diaphragm button and an aperture for displaying an LED. The button is arranged to contact a corresponding button on the battery housing or PCB to activate the device. The aperture displays an LED which indicates whether the device is operating.

As described in WO2010/070332, the device and similar devices may be used for a range of medical and other conditions, for example reduction or treatment of deep vein thrombosis (DVT), to improve circulation, to increase venous emptying in the leg, and to increase cortical blood flow in the long bones of the leg. Due to these effects, the device is suggested for use to treat conditions characterised by impaired venous blood flow, including ulcers, varicose veins, ischaemia, oedema, phlebitis, osteoporosis, peripheral vascular disease, coronary heart disease, and hypertension. These disorders are considered to be treatable on the basis that the device and method can increase venous blood flow.

To use the device, the electrodes are secured to the leg of a patient and used to provide electrical stimulation to the muscles. Preferably the electrodes are arranged to stimulate the lateral and/or medial popliteal nerves, which causes the calf muscles to contract. This in turn activates the calf musculovenous pump, in which blood circulation is promoted by muscle contraction, so serving to reduce the risk of thrombosis in the limb. Other musculovenous pumps include the foot pump, and the device may be used to stimulate this as well as, or instead of, the calf pump. The device is preferably used to induce isometric contraction of the muscles, such that the musculovenous pumps may be activated but limb movement from the stimulation is reduced or avoided.

Figure 2:
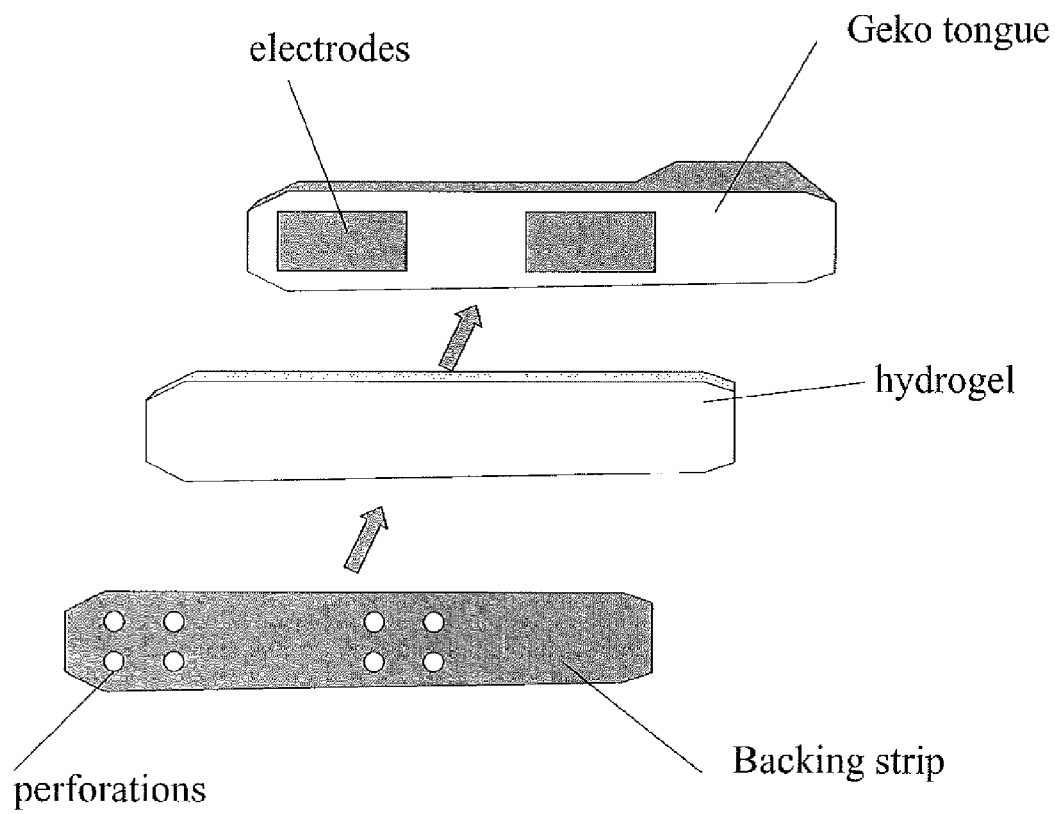
FIG. 2 shows a schematic diagram of an embodiment of a device according to a first aspect of the present invention.

FIG. 2 shows the modified device according to an embodiment of the present invention. The device itself may be as shown in FIG. 1, and includes a layer of hydrogel or other gel material which serves to adhere the device to a user's skin, and to provide electrical contact between the skin and the electrodes. Over the hydrogel is placed a perforated backing strip, which serves to protect the hydrogel when the device is not in use, or is in transit. The perforations allow a small portion of the hydrogel to contact the skin through the backing strip, so permitting a small amount of current to flow despite the presence of the strip.

The intention is to provide a partially conductive backing strip. This may be achieved through the use of particular materials to form the strip, but a practical, convenient, reliable and inexpensive means of providing a partially conductive backing is to provide perforations in the backing strip. This has advantages in that it requires no special material. A further advantage is that there will be conduction only through the perforations, not along the length of the strip between electrodes.

To use the device, the device including the strip is placed on a user's skin, and activated. As current flows, the device may be moved around the skin to determine the optimum position for such stimulation as is desired. Once the correct location is found, the position of the device is marked, the backing strip removed, and the device replaced with the whole of the hydrogel layer contacting the skin and serving to retain the device in position.

In the preferred embodiment, see FIG. 2, only a small proportion of the surface of the backing strip is perforated. By experiment, we determined that optimal position may be found with only limited conductivity through the backing strip. Only the relatively small 'dots' of gel exposed during 'scanning' experience any deterioration, and the adhesive and conductive properties of the gel strip as a whole are negligibly affected.

During the process of locating the optimal position (referred to as "scanning"), an alcohol solution or alcohol gel may be applied to the user to aid movement of the device across the skin. By experimentation, we found that this was sufficiently conductive, quick-drying, and beneficially cleaned the skin prior to application of the device (after removal of perforated backing strip). Alternatively the backing strip may include a lubricant on the outer surface.

Other variations of the device may include different sizes, shapes, numbers, and arrangements of perforations; the use of separate strips with small gaps between, instead of holes; the whole strip being uniformly perforated (which gives possible sourcing and manufacturing advantages); the use of a double backing (an additional low-tack backing strip over the perforated strip, to protect gel at holes); the packaging of devices back-to-back in pairs to protect gel at holes; and the presence of notches, etc in the device to aid marking registration points.

Figure 3:
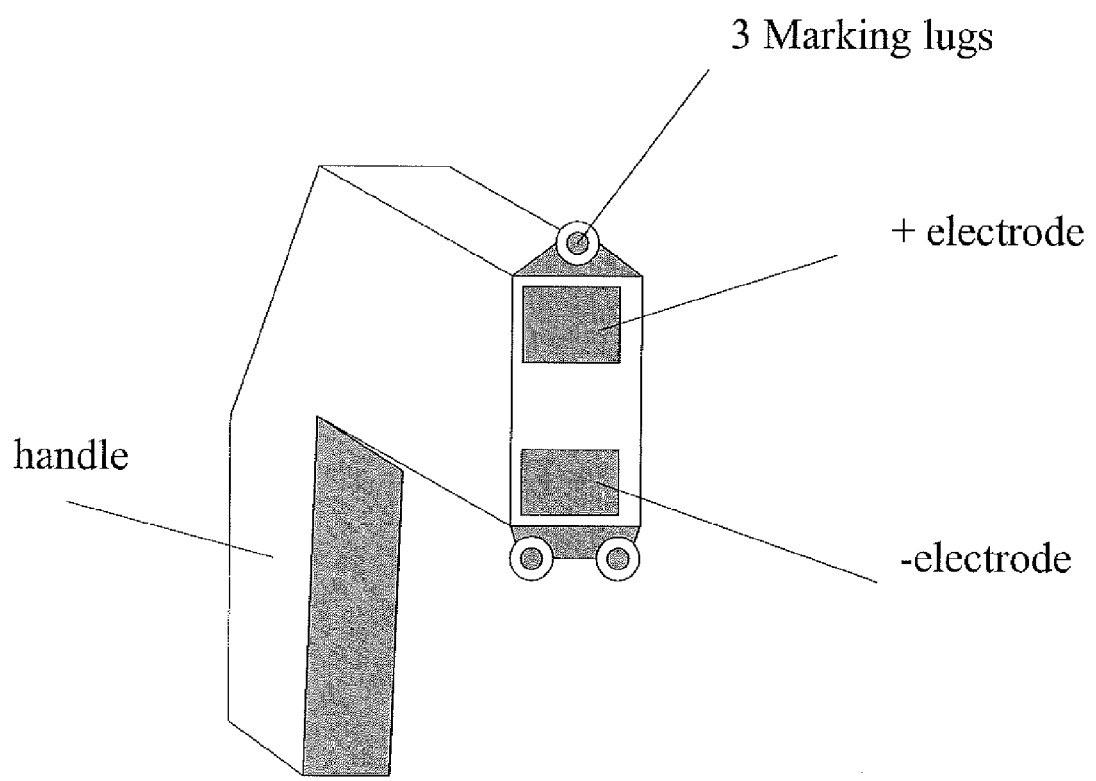
FIG. 3 shows a sketch of a further embodiment of a device according to another aspect of the present invention.

A second embodiment of a locator device is shown in FIG. 3. This takes the form of a rigid substrate having a handle, with a pair of electrodes being mounted on the substrate in the same configuration (that is, size, shape, and location) as the electrodes on the working electrical stimulation device. This locator device could be used to 'scan' the relevant region of the patient, having first prepared the skin with a suitable conductive aqueous or alcohol gel. Having found the correct location, this could then be marked using the marking lugs of the locator. For example, the locator may include a trigger which actuates the lugs to make a mark on the skin, or the locator may simply be pressed firmly against the skin such that the lugs make a temporary mark. After this the locator is removed, and a working stimulator device positioned in the correct location.

The invention claimed is:

1. A device for administering electrical stimulation to a patient, the device comprising a pair of electrodes located on a flexible substrate, a power supply connectable to the electrodes, and control means for actuating the electrodes, wherein the device further comprises a conductive gel layer overlying the electrodes, and a removable cover overlying the conductive gel layer, wherein the removable cover is at least partially conductive such that electrical contact may be formed in use between the electrodes and a patient when the cover is in place.

2. The device of claim 1 wherein the gel is in a single piece overlying both electrodes.

3. The device of claim 1 wherein the power supply and/or the control means are also located on the flexible substrate.

4. The device of claim 1 wherein the substrate comprises one or more registration marks, to allow a user to mark the location of the device prior to removal and replacement.

5. The device of claim 1 wherein the cover is a removable strip which conforms to the shape of the substrate.

6. The device of claim 1 wherein the cover is less conductive than the conductive gel.

7. The device of claim 1 wherein the cover is formed of a partially conductive material.

8. The device of claim 1 wherein the cover comprises perforations which allow a portion of the conductive gel to be contacted through the cover.

9. The device of claim 8 wherein the perforations are generally uniformly distributed over the cover.

10. The device of claim 1 wherein the cover further comprises a lubricant coating to reduce friction between a user's skin and the cover when moving the device.

11. The device of claim 1 wherein the cover is in the form of a second conductive or partially conductive gel, of different composition to the first conductive gel.

12. The device of claim 1 comprising an additional removable protective cover, preferably in the form of a protective strip, to cover the first cover.

13. A package comprising a pair of devices as described in claim 1 wherein the devices are placed such that the cover of one contacts the cover of the other.

* * * * *